United States Patent [19]
Gallagher

[11] 3,957,864
[45] May 18, 1976

[54] PROCESS FOR RECOVERY OF 1-GLUTAMIC ACID

[75] Inventor: John S. Gallagher, Paris, Ill.

[73] Assignee: Commercial Solvents Corporation, Terre Haute, Ind.

[22] Filed: Mar. 31, 1975

[21] Appl. No.: 563,755

[52] U.S. Cl. .................................. 260/534 G
[51] Int. Cl.² ............................... C07C 99/12
[58] Field of Search ..................... 260/534 G

[56] References Cited
UNITED STATES PATENTS

| | | | |
|---|---|---|---|
| 2,683,739 | 7/1954 | Weidman | 260/534 G |
| 3,360,554 | 12/1967 | Yamamoto et al. | 260/534 G |
| 3,365,492 | 1/1968 | Noyori et al. | 260/534 G |

OTHER PUBLICATIONS

Sakata, "Agr. Biol. Chem.," Vol. 25 (1961), parts I and II, pp. 829–837.
Sakata, "Agr. Biol. Chem.," Vol. 26 (1962), part III, pp. 355–361.
Sakata et al., "Agr. Biol. Chem.," Vol. 26 (1962), part IV, pp. 816–823.
Sakata et al., "Agr. Biol. Chem.," Vol. 27 (1963), part V, pp. 133–142.

*Primary Examiner*—Joseph E. Evans
*Attorney, Agent, or Firm*—Robert H. Dewey; Howard E. Post

[57] ABSTRACT

An improved process for recovering 1-glutamic acid from an aqueous solution containing it by the steps of adjusting the pH of the solution to about 4.5, at ambient temperature, holding at that pH until crystals of 1-glutamic acid begin to appear, heating to from 47° to about 55°C, adjusting the pH to 3.2, cooling, and recovering the crystals resulting therefrom.

1 Claim, 6 Drawing Figures

FIG.1
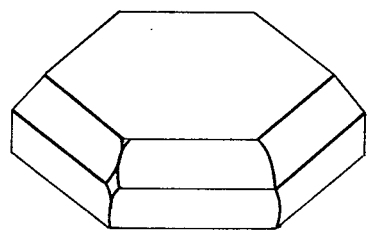
FIG.2
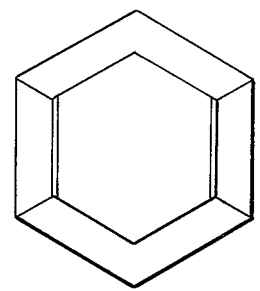
FIG.3
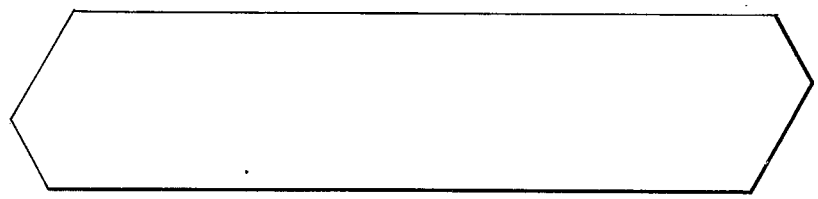
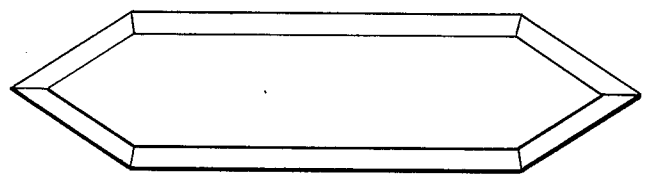
FIG.4
FIG.5
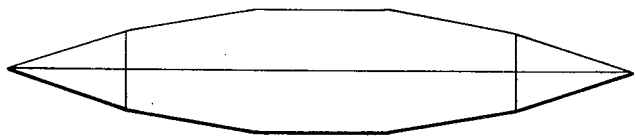
FIG.6

PROCESS FOR RECOVERY OF 1-GLUTAMIC ACID

BACKGROUND OF THE INVENTION

This invention relates to a method of recovering 1-glutamic acid from a solution containing it. In a particular aspect this invention relates to a method of changing the crystal habit of 1-glutamic acid.

1-Glutamic acid in the form of its monosodium salt is an important flavor-enhancing material for foods and is widely used in the preparation of processed foods. One method of preparation is by cultivating an 1-glutamic acid-producing micro-organism, e.g. *Brevibacterium divaricatum*, on a nutrient fermentation medium, as is known in the art, until the glutamic is produced. When the fermentation is complete, the resulting broth containing the 1-glutamic acid is treated to crystallize the 1-glutamic acid, then centrifuged to separate the broth and the cells of the micro-organism. It is also known to filter the broth to remove the cells prior to crystallization of the 1-glutamic acid.

It is known from J. D. Bernal, Z. Kryst 78, 363 (1931) and S. Hirokawa, Acta. Cryst., 8, 637 (1955) that 1-glutamic acid occurs in two crystal forms, designated $\alpha$ and $\beta$. When a saturated aqueous solution of 1-glutamic acid at 70°C is cooled rapidly, granular or prismatic crystals, the $\alpha$-form, are obtained. This crystal form is shown in FIG. 1 and FIG. 2, top view. $\alpha$-Crystals are hexagonal in cross-section with a diameter several times the thickness. They would be ideal for industrial processes because of their ease of handling. However their formation on a large scale is difficult and they rearly occur under processing conditions.

On the other hand when a saturated solution of glutamic acid at 90° is cooled gradually so that crystallization occurs at 40°–50°C, needle-like or flaky crystals, the $\beta$-form, are obtained. This form is shown in FIGS. 3 and 4. It is the one commonly encountered in industrial processing. The $\beta$-crystals are long and flat, i.e. the width and length are much greater than the depth.

These two crystal forms were the subject of an investigation by Yoshiki Sakata reported in a series of papers in Agr. Biol. Chem. 25,829–837 (1961); 26,355–361 (1962); 26,816–823 (1962) and 27,133–142 (1963), which are incorporated herein by reference. Sakata reported that the $\alpha$-form was less soluble than the $\alpha$-form and as a result, slurries of the $\alpha$-form gradually changed into slurries of the $\beta$-form.

These plate-like $\beta$-crystals pack easily during filtration and hinder additional filtration. Also they do not centrifuge well because they tend to break up, pack and trap impurities in the crystal cake and are difficult to wash. Consequently there is a need for a method of changing the growth habit of glutamic acid crystals to a form which can be more easily filtered or centrifuged.

SUMMARY OF THE INVENTION

It is an object of this invention to provide an improved method of recovering 1-glutamic acid from a solution containing it.

It is another object of this invention to provide a method of changing the growth habit of crystals of 1-glutamic acid.

Other objects will be apparent to those skilled in the art from the disclosure herein.

An improved process for the recovery of glutamic acid from a solution containing it has been discovered wherein the glutamic acid is crystallized in a changed crystal habit. The improved process comprises the steps of adjusting at room temperature the pH of a fermentation broth containing glutamic acid to pH 4.5 maintaining the pH thereat until seed crystals begin to appear, heating to about 55°C, preferably to within 47°–53°C and adjusting the pH to 3.2. The crystals of glutamic acid thereby obtained exhibit a different form than those obtained by the prior process. The new crystals are of a distinctive shape being pointed at each end and thicker in the center than at the ends. They are hexagonal in cross-section and exhibit different solubility characteristics. The new crystals do not break-up during centrifuging and can be easily washed. They do not pack tightly on the filter bed and therefore are easily filtered.

With reference to the drawing,

FIG. 1 shows the $\alpha$-crystal in ¾ side view and

FIG. 2 shows the view from the top.

FIGS. 3 and 4 show 2 views of the $\beta$-crystal which is flat and thin.

FIGS. 5 and 6 show a top and side view of the new crystal form, herewith designated the $\gamma$-form.

DETAILED DISCUSSION

The glutamic acid solution employed in the practice of this invention is peferably but not necessarily, a fermentation broth, filtered or unfiltered. The concentration of the glutamic acid in solution should be above 60 g per liter for good recovery. If it is less than that, the solution is concentrated by any suitable method, e.g. by evaporation. The temperature is brought to ambience, e.g. about 20°, if necessary, and the pH is adjusted to about 4.5 at such a rate of acid addition that the ambient temperature is maintained. The pH adjustment can be effected with any suitable acid, many of which are knwon, e.g. with sulfuric, hydrochloric or nitric acid. Sulfuric acid is usually preferred. If the pH is below 4.5, it is adjusted upward with a suitable alkaline material, e.g. alkali or alkaline earth hydroxides or carbonates, or ammonia or the lower aliphatic amines. Ammonia is preferred.

The solution is maintained at pH 4.5 at ambient temperatures, e.g. about 20°C, with constant agitation until it is determined that seed crystals have begun to form. Then it is heated to within about 47°–55°, preferably about 50°. Care is taken to avoid raising the temperature above 55°C, because it has been found that crystals formed after heating above that temperature are the $\beta$-form. The pH is then lowered to the isoelectric point, within pH 2.8–3.4, preferably 3.2. The temperature is then reduced to 20°C with agitation during which time the glutamic acid continues to crystalize. Additional adjustments of pH are made as necessary to maintain the range 2.8–3.4. Most, i.e. about 70–80%, of the crystals will be of the new $\gamma$-form, with about 20–30% in the old, platelet $\beta$-form.

Afte crystallization is complete, the crystals are recovered by any suitable method, e.g. by decantation, or preferably by centrifugation or filtration. The glutamic acid so recovered is then converted to food-grade monosodium glutamate by any suitable method, many of which are known.

The invention will be better understood with reference to the following example. It is understood that the example is intended for illustration only and it is not intended that the invention be limited thereby.

EXAMPLE l-Glutamic acid is produced by fermentation to form a broth. When fermentation is judged to be complete, the broth is concentrated by evaporation to produce a concentration of 70 g/liter. It is then cooled to about 30°C and sulfuric acid is added with agitation at a rate such as not to result in a temperature rise to produce a pH of about 4.5. After pH adjustment, the agitation is continued until a sample shows that seed crystals have begun to form (about 20 minutes is required). The broth is then heated to about 50°C and sulfuric acid solution again is added until the pH is about 3.2. The broth is then cooled to about 20°C with agitation. The pH is monitored during the cooling step and is adjusted with more acid as necessary.

During the cooling step the l-glutamic acid crystallizes in the γ-form. It is separated by centrifugation, washed with water and again centrifuged and dried. When viewed under a microscope it is observed that about 75% of the crystals are of the γ-form and about 25% are of the β-form.

The l-glutamic acid produced as above is converted to the monosodium salt with sodium hydroxide, then crystallized. The color of the crystals is less than by the prior process due to more efficient washing made possible by the crystal form.

I claim:

1. An improved method for recovering l-glutamic acid from a solution containing it by the steps of adjusting the pH of an aqueous solution containing glutamic acid to about 4.5 while maintaining ambient temperature, holding the solution with agitation until crystals begin to appear, heating to within 47° to 55°, adjusting the pH to about 3.2, cooling to about 20°C thereby causing the l-glutamic acid to crystallize in a changed crystal form, and recovering same by centrifugation, filtration or decantation.

* * * * *

UNITED STATES PATENT OFFICE
CERTIFICATE OF CORRECTION

Patent No. 3,957,864             Dated May 18, 1976

Inventor(s) John B. Gallagher

It is certified that error appears in the above-identified patent and that said Letters Patent are hereby corrected as shown below:

Column 1, line 15, "glutamic" should read -- glutamic acid --

Column 1, line 33, "rearly" should read -- rarely --

Column 1, line 35, "90°" should read -- 90°C --

Column 1, line 47, "α-form" should read -- β-form --

Column 2, line 27, "peferably" should read --preferably --

Column 2, line 37, "knwon" should read -- known --

Column 2, line 59, "afte" should read -- after --

Signed and Sealed this

Twenty-first Day of June 1977

[SEAL]

Attest:

RUTH C. MASON
Attesting Officer

C. MARSHALL DANN
Commissioner of Patents and Trademarks